(12) United States Patent
Kok et al.

(10) Patent No.: US 10,682,106 B2
(45) Date of Patent: Jun. 16, 2020

(54) VARIABLE FOCUS X-RAY ANTI SCATTER DEVICE

(71) Applicant: KONINKLIJKE PHILIPS N.V., Eindhoven (NL)

(72) Inventors: Christiaan Kok, Noord-Brabant (NL); Johannes Wilhelmus Maria Jacobs, Boxtel (NL); Robertus Marinus Wilhelmus Raaijmakers, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/321,524

(22) PCT Filed: Aug. 25, 2017

(86) PCT No.: PCT/EP2017/071476
§ 371 (c)(1),
(2) Date: Jan. 29, 2019

(87) PCT Pub. No.: WO2018/037128
PCT Pub. Date: Mar. 1, 2018

(65) Prior Publication Data
US 2019/0343471 A1    Nov. 14, 2019

(30) Foreign Application Priority Data
Aug. 25, 2016   (EP) ..................................... 16185625

(51) Int. Cl.
*G02B 1/04*       (2006.01)
*A61B 6/00*       (2006.01)
*G21K 1/02*       (2006.01)

(52) U.S. Cl.
CPC .............. *A61B 6/4291* (2013.01); *G02B 1/04* (2013.01); *G21K 1/025* (2013.01)

(58) Field of Classification Search
CPC ......... A61B 6/4291; G02B 1/04; G21K 1/025
See application file for complete search history.

(56) References Cited

U.S. PATENT DOCUMENTS

| 4,340,818 A * | 7/1982 | Barnes ...................... A61B 6/06 |
| | | 378/155 |
| 5,291,539 A | 3/1994 | Thumann |
| 5,594,769 A * | 1/1997 | Pellegrino .............. A61B 6/502 |
| | | 378/208 |
| 5,999,836 A | 12/1999 | Nelson |

(Continued)

FOREIGN PATENT DOCUMENTS

| DE | 102011076875 A1 | 12/2012 |
| DE | 102012217965 A1 | 4/2014 |
| DE | 102013204269 | 9/2015 |

*Primary Examiner* — Hugh Maupin
(74) *Attorney, Agent, or Firm* — Larry Liberchuk (57) ABSTRACT

An anti-scatter device (10) for an X-ray detector (100) is provided. The anti-scatter device (10) comprises an anti-scatter grid (12) with a plurality of slats (13) for absorbing X-rays and a cover element (14, 14a) arranged on a side (17a) of the anti-scatter grid (12), wherein ends (16a) of the slats (13) are coupled to the cover element (14, 14a), and the cover element (14, 14a) comprises an electroactive polymer material. A dimension of the cover element (14, 14a) is changeable by applying a voltage to the electroactive polymer material, such that a distance between the ends (16a) of the slats is changeable by applying the voltage.

14 Claims, 6 Drawing Sheets

(56) References Cited

U.S. PATENT DOCUMENTS

| | | |
|---|---|---|
| 6,470,072 B1 | 10/2002 | Johnson |
| 7,127,038 B2 | 10/2006 | Komdradsson |
| 7,206,382 B2 | 4/2007 | Besana |
| 2004/0251419 A1 | 12/2004 | Nelson |
| 2008/0063138 A1 | 3/2008 | Levene |
| 2012/0169184 A1* | 7/2012 | Pelrine .................. H01L 41/45 310/365 |
| 2013/0176608 A1* | 7/2013 | Brokken ............ G02B 26/0825 359/224.1 |
| 2013/0202091 A1 | 8/2013 | Haider |
| 2013/0235972 A1 | 9/2013 | Kuroiwa |
| 2015/0043079 A1 | 2/2015 | Park |

* cited by examiner

VARIABLE FOCUS X-RAY ANTI SCATTER DEVICE

FIELD OF THE INVENTION

The invention generally relates to the field of radiation detectors. More specifically, the invention relates to an anti-scatter device for an X-ray detector, an X-ray detector with such anti-scatter device and a method for producing an anti-scatter device.

BACKGROUND OF THE INVENTION

An image quality of X-ray images generally may be limited in X-ray detectors and/or in X-ray imaging systems with a variable source-image-distance. In order to improve the image quality, usually an anti-scatter device comprising an anti-scatter grid is utilized, which allows to increase a contrast in the X-ray image by reducing an incidence of scattered radiation upon a reception area of the X-ray detector.

Examples of such X-ray system is for instance a C-arm system, in which an assembly comprising an X-ray detector and an anti-scatter device and/or an anti-scatter grid may be moved closer to and/or further away from an X-ray source. In other X-ray imaging systems with variable source-image-distance the X-ray source may be moved closer to and/or further away from an assembly comprising a table and an X-ray detector with anti-scatter device depending on application demands and/or requirements. In all these systems, usually a less than optimal anti-scatter grid ratio needs to be chosen to reduce the detrimental effects of shading artifacts caused by the grid when operated with a source-image-distance differing from its nominal focal distance. In the international norm IEC60627 the application limits for given grid parameters are provided and these limits should be matched with customer wishes for the range of allowed source-image-distances.

A potential solution to this issue may be to have a variable focused anti-scatter grid in which a focal distance and/or a focusing distance may be matched to the actual source-image-distance for a certain range of source-image-distances. For such grids a higher aspect ratio, as defined in IEC60627, may be chosen which may reduce the amount of scattered radiation in the X-ray image and thus may improve the image quality.

Normally, an anti-scatter device and/or an anti-scatter grid comprises a stack of lead lamellae interspaced with an X-ray transparent interspacer material, such as air, an organic material and/or Aluminum, which positions each lead lamella in an orientation directed towards a focal spot of the anti-scatter device and/or the anti-scatter grid at a distance equal to the focal distance and/or the focusing distance. Further, the anti-scatter device and/or the anti-scatter grid may be covered with a carbon fiber or an aluminum cover element to give the grid sufficient stiffness and to protect the interior against moisture and harm.

In document U.S. Pat. No. 5,291,539 A a variable focused anti-scatter grid is disclosed having a flexible elongated slatted grid structure, which is suspended between a pair of spaced apart grid support frames each of which is adapted for rotation about a transverse axis intermediate the suspended ends of the grid. A mechanical adjustment means provides equal but opposite angular motion of the frames to curve the grid along a circular path.

SUMMARY OF THE INVENTION

There may therefore be a need for a compact, reliable, robust, easily controllable, easily adjustable and cost efficient anti-scatter device and for an X-ray detector with such anti-scatter device.

The object of the present invention is solved by the subject matter of the independent claims, wherein further embodiments are incorporated in the dependent claims and the following description.

According to a first aspect of the invention, an anti-scatter device for an X-ray detector is provided. The anti-scatter device comprises an anti-scatter grid with a plurality of slats for absorbing X-rays and/or photons and/or X-ray photons. Further, the anti-scatter device comprises a cover element arranged on a side and/or on an outer surface of the anti-scatter grid. Therein, ends of the slats are coupled, e.g. mechanically coupled, to the cover element. Further, the cover element comprises an electroactive polymer material, wherein a dimension of the cover element is changeable, variable and/or increasable by applying and/or varying a voltage to the electroactive polymer material, such that a distance between the ends of the slats is controllable, increasable, variable and/or changeable by applying and/or varying the voltage.

The anti-scatter grid may particularly refer to a variable focused anti-scatter grid, i.e. to a focused grid with variable and/or adjustable focusing distance. Generally, as e.g. defined in the international norm IEC60627, a focused grid may refer to a grid, in which planes of the X-ray absorbing slats converge to a straight line at the focusing distance. Accordingly, the focusing distance may refer to the distance between an incident face of a focused grid and the line into which planes of the absorbing slats converge.

The slats may refer to strips, lamellae, bars and/or tube-shaped elements comprising X-ray absorbing material, such as e.g. lead (Pb), molybdenum (Mo), tungsten (W) and/or a compound thereof.

The cover element may generally refer to any mechanical support structure for mechanically supporting the slats. For instance, the cover element may refer to a plate-like structure, e.g. a cover plate, and the ends of the slats may be coupled to and/or arranged on a side of the cover plate and/or the cover element. The ends of the slats may be mechanically coupled to the cover element by any suitable fixation means. For instance, the ends may be glued and/or welded and/or soldered to the cover element. The slats may be arranged on and/or coupled to the cover element such that they extend transversely from the cover element and/or from a side thereof.

Further, the slats of the anti-scatter grid may be spaced-apart from each other by interspacers, interspacer material and/or air. The interspacers and/or the interspacer material may be pliable to allow changing the distance between the ends of the slats. The interspacers and/or the interspacer material may comprise X-ray transparent material, such as e.g. fiber material, polymer material, or the like.

The electro-active polymer material, also referred to as piezo-active polymer material, may refer to a polymer material and/or a polymer which can have a dimensional change induced by an electric field, a voltage and/or a potential difference applied to and/or across the electroactive polymer material. In other words, an extension of the electro-active polymer material may be induced and/or the electro-active polymer material may be expanded by applying a voltage. Accordingly, a length and/or a size of the electro-active polymer material may be changed, controlled and/or increased by applying the voltage. The applied voltage may be in the kV range.

Rephrasing the first aspect, the X-ray absorbing slats are arranged on and/or attached to the cover element such that they extend transversely from the cover element and/or transversely from a side of the cover element. By applying a voltage, an electric field, a potential and/or a potential difference to the electro-active polymer material a length, a size and/or the dimension of the cover element may be changed and/or increased at least in one direction. Thus, by applying the voltage to the electro-active polymer material an extension of the cover element may be induced and/or the cover element may be expanded at least in one direction. More specifically, the dimension, size and/or length of the cover element may be proportional to the amount and/or level of voltage applied. Hence, the dimension, size and/or length of the cover element may be varied by varying the applied voltage. Therefore, with respect to no voltage applied initially, the dimension, size and/or length of the cover element may be increased, whereas with respect to an initially applied voltage a reduction of the voltage may lead to a reduction of the dimension, the size and/or the length of the cover element. In other words with respect to an initially applied voltage, the cover element may shrink when the voltage is reduced. Further, since the ends of the slats are coupled and/or fixed to the cover element, the distance between the ends of the slats is also changed and/or increased. This may also lead to a change in the orientation and/or an extension direction of at least a part of the slats. As a consequence, the focusing distance of the anti-scatter grid and/or the anti-scatter device may be changed and/or adjusted by applying the voltage to the electro-active polymer material.

According to an embodiment, at least a part of the anti-scatter device is bendable by applying the voltage to the electroactive polymer material of the cover element. For instance, at least an outer surface of the cover element may be bendable. Accordingly, by applying the voltage, a curvature of at least a part of the anti-scatter device is adjustable and/or inducable by applying the voltage. This may allow to bend the anti-scatter device and/or the anti-scatter grid from a flat shape to a curved shape by applying the voltage. Therefore, using the electro-active polymer material for the cover element of the anti-scatter device may provide the possibility to steer the cover element's dimension and thereby change and/or adapt a radius of the curvature of the anti-scatter grid. Further, by changing the radius of the curvature the focal distance and/or the focusing distance of the anti-scatter grid may be influenced, controlled and/or changed. This may allow to adjust a focal/focusing distance equal to a source-image-distance within a certain range of source-image-distances in order to improve an image quality. This may further alleviate difficult mechanics of commonly used variable focused anti-scatter grids. Also, by using the electro-active polymer material a cost efficient anti-scatter device may be provided.

The invention may generally be considered being based on the following findings and insights. In imaging systems with a variable source-image-distance the anti-scatter grid function of a conventional non-flexible anti-scatter grid may be hampered at source-image-distance settings which differ from the nominal grid focus and/or the nominal focusing distance of the anti-scatter grid. As a compromise, parameters of the anti-scatter grid, most notably the grid ratio, may be chosen relatively low, so that grid functioning at the edges and/or borders of the allowed source-image-distance range may be acceptable, wherein the grid ratio may refer to the ratio between a height of the slats and a distance between the slats. This may reduce an overall performance of the anti-scatter grid and/or the anti-scatter device. Thus, the anti-scatter device may be less selective for discriminating primary from secondary, i.e. scattered, radiation than it would be for a single fixed source-image-distance system. Therefore, by controlling and/or changing the distance between the ends of the slats of the inventive anti-scatter device, and/or the focusing distance may be changed according to a required source-image-distance. This may allow to acquire images of constant quality over a rather broad range of source-image-distances.

According to an embodiment, the cover element comprises at least one layer or a plurality of layers of the electroactive polymer material. The layers of electroactive polymer, which may be referred to hereinafter as electroactive polymer layers, may be stacked on top of each other, wherein edges of the layers may be flush, aligned and/or shifted with respect to each other.

According to an embodiment, the cover element comprises at least one electrode or a plurality of electrodes for applying the voltage. Generally, this may increase a flexibility of the anti-scatter device in terms of providing the possibility to contact the electroactive polymer at various locations and/or regions. Also, voltages differing in size and/or sign may be applied by means of the plurality of electrodes.

According to an embodiment, the plurality of electroactive polymer layers and the plurality of electrodes are alternately arranged. Particularly, the electroactive polymer layers and the electrodes may be alternately stacked on top of each other in a sandwich-like or multi-stack structure. Generally, such multi-stack structure may reduce the voltage required for a certain radius of a curvature of the anti-scatter grid and/or required for a certain change in dimension of the cover element.

According to an embodiment, the electroactive polymer material comprises at least one monomer selected from the group consisting of Vinylidene-Fluoride and Trifluorovinyl.

According to an embodiment, the electroactive polymer material comprises at least one of Polyvinylidene-Fluoride (PVDF) and Polytrifluorovinyl (PTFV) or a copolymer thereof. Also any other electroactive polymer material may be used as material for the cover element. However, the cover element may also comprise other material. E.g. the cover element may comprise any other flexible polymer material in addition to the electroactive polymer.

According to an embodiment, the cover element is formed as a foil. For instance, the cover element may be formed as monolithic and/or flexible foil. Generally, this may reduce a number of parts, simplify production, reduce production cost and increase robustness of the cover element and/or the anti-scatter device.

According to an embodiment, the anti-scatter device further comprises a further cover element, wherein the anti-scatter grid is arranged between the cover element and the further cover element. Further ends of the slats are coupled, particularly mechanically coupled, to the further cover element. The further ends of the slats may oppose the ends of the slats with respect to a longitudinal extension and/or a longitudinal extension direction of the slats. The further ends may be glued, welded and/or soldered to the further cover element and/or to a side thereof. Thus, the slats may extend, e.g. transversely, from the cover element to the further cover element.

According to an embodiment, the further cover element is rigid. Therein, "rigid" may mean that the further cover element may not be elastically deformed by any deformation of the cover element potentially induced by applying a voltage to the cover element. E.g. the further cover element may comprise metal, fiber material and/or plastic material.

According to an embodiment, the further ends of the slats are fixed at and/or fixedly attached to the further cover element. Generally, this may allow to increase and/or change a distance between the ends of the slats coupled to the cover element while maintaining a constant distance between the further ends of slats coupled to the further cover element. Accordingly, a trapezoidal shape of the anti-scatter device may be induced by applying a voltage to the cover element, thereby changing a focusing distance of the anti-scatter grid.

Also, the anti-scatter grid may be a parallel grid when no voltage is applied to the cover element, i.e. the slats may be arranged parallel with respect to each other. By applying the voltage, a focused grid may be provided.

According to an embodiment, the further cover element comprises electroactive polymer material, wherein a dimension of the further cover element is changeable, variable and/or increasable by applying and/or varying a voltage to the electroactive polymer material of the further cover element, such that a distance between the further ends of the slats is controllable, variable, changeable and/or increasable by applying and/or varying the voltage. In other words, the cover element and the further cover element may comprise electroactive material, such that a distance between the ends and the further ends of the slats may be changed, varied and/or increased by applying and/or varying the voltage. Therein, equal or differing voltages may be applied to the cover element and the further cover element. Generally, this may further increase a variability of the anti-scatter device in terms of allowing to change the shape of the anti-scatter grid.

A further aspect of the invention relates to an anti-scatter arrangement. The anti-scatter arrangement comprises a plurality of anti-scatter devices as described above and in the following. The anti-scatter devices of the anti-scatter arrangement may be arranged on top of each other in an arbitrary orientation and/or in an arbitrary angle with respect to each other. Particularly, the anti-scatter arrangement may comprise two anti-scatter devices, e.g. providing a cross-grid, an orthogonal cross-grid, and/or an oblique cross-grid. The anti-scatter grids of the anti-scatter arrangement may be arranged at an arbitrary angle with respect to a pixel structure of a radiation detector. Further, the anti-scatter grids of the anti-scatter devices may also be arranged next to each other, i.e. in juxtaposition, allowing to increase an overall area and/or size of the anti-scatter device.

It should be noted that features and/or elements of the anti-scatter device may be features and/or elements of the anti-scatter arrangement and vice versa.

A second aspect of the invention relates to the use of an electroactive polymer material in an anti-scatter device for adjusting a focusing distance of an anti-scatter grid of the anti-scatter device by applying a voltage to the electroactive polymer material. More specifically, the electroactive polymer may be used as material for at least one cover element of the anti-scatter device and/or the anti-scatter grid. Generally, the anti-scatter device may comprise any features and/or elements as described above and in the following.

A third aspect of the invention relates to an X-ray detector comprising at least one anti-scatter device as described above and in the following.

It should be noted that features and/or elements of the X-ray detector may be features and/or elements of the anti-scatter device and vice versa.

According to an embodiment, the X-ray detector further comprises a flexible substrate foil, which may e.g. comprise polyimide material or the like. The X-ray detector further comprises an array of pixels, e.g. photosensitive pixels, arranged on the substrate foil and configured for detecting X-rays. Moreover, the X-ray detector comprises a scintillator arranged on the array of pixels, wherein the anti-scatter device is arranged on the scintillator, and the anti-scatter grid is arranged between the cover element of the anti-scatter device and the scintillator. Therein, at least a part of the X-ray detector is bendable by applying the voltage to the electroactive polymer material of the cover element. This may mean that only the anti-scatter device and/or only the anti-scatter grid may be bendable by applying the voltage. Alternatively, also other elements and/or the entire X-ray detector may be bendable. According to an embodiment, the substrate foil comprises electroactive polymer material, wherein the X-ray detector is bendable by applying a voltage to the electroactive polymer material of the substrate foil.

According to an embodiment, the X-ray detector further comprises a layer, e.g. a flexible foil layer, comprising electroactive polymer material. The layer may be arranged e.g. between the anti-scatter grid and the scintillator or on an outer surface of the X-ray detector.

According to a fourth aspect of the invention, a method for producing an anti-scatter device is provided. The method comprises the following steps:

providing an anti-scatter grid with a plurality of slats for absorbing X-rays;

arranging a cover element on a side of the anti-scatter grid, such that the slats extend transversely from the cover element; and coupling ends of the slats to the cover element.

Therein, the cover element comprises an electroactive polymer material and a dimension of the cover element is changeable and/or increasable by applying a voltage to the electroactive polymer material, such that a distance between the ends of the slats is controllable, changeable and/or increasable by applying the voltage.

It should be noted that features and/or elements of the anti-scatter device and/or the X-ray detector may be features, elements and/or steps of the method. Vice versa, features, elements and/or steps of the method may be features and/or elements of the anti-scatter device and/or the X-ray detector.

These and other aspects of the invention will be apparent from and elucidated with reference to the embodiments described hereinafter.

BRIEF DESCRIPTION OF THE DRAWINGS

The subject matter of the invention will be explained in more detail in the following with reference to exemplary embodiments which are illustrated in the attached figures, wherein.

In principle, identical and/or similar parts are provided with the same reference symbols in the figures. The figures are not to scale.

DETAILED DESCRIPTION OF EMBODIMENTS

Figure 1:
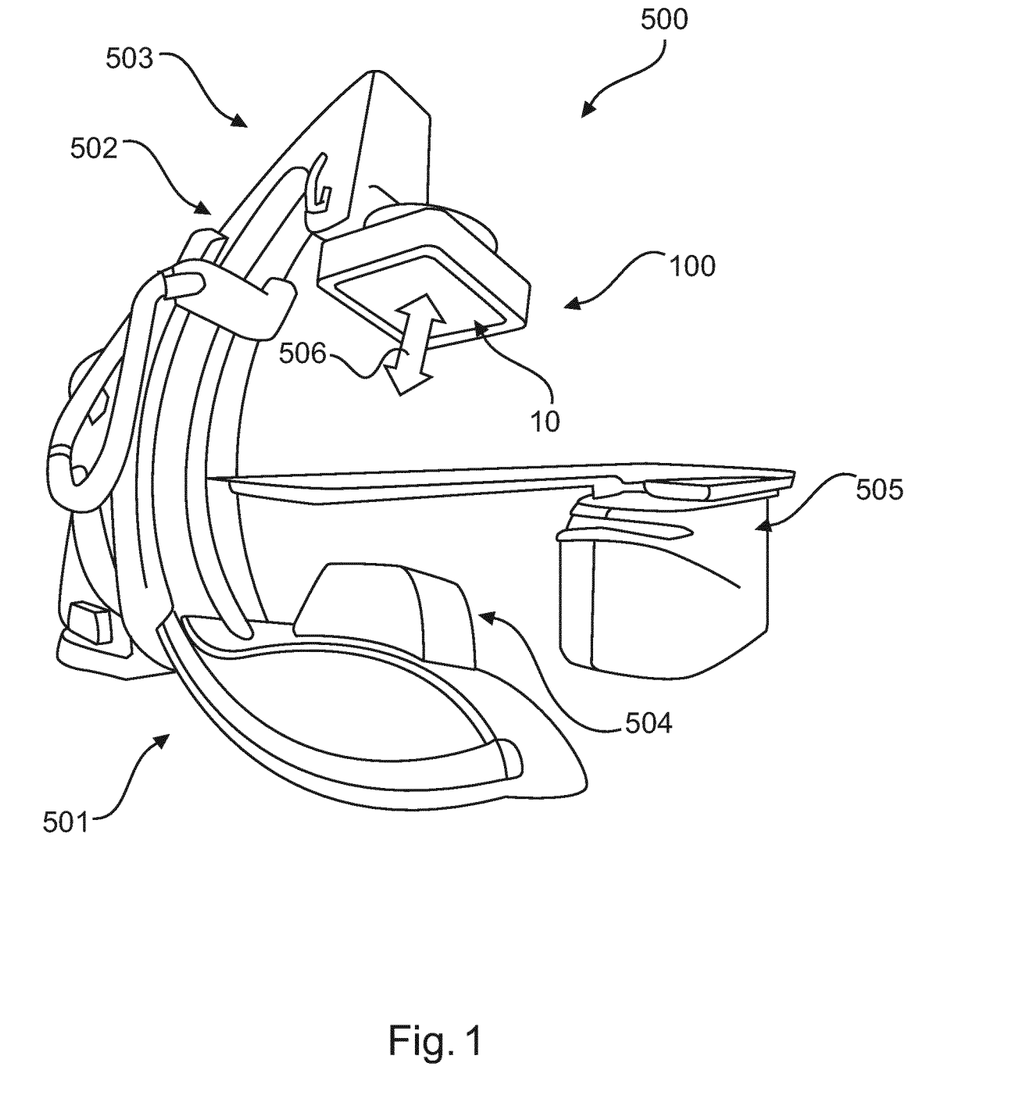
FIGS. 1 and 2 each show schematically a perspective view of an X-ray imaging system.

FIG. 1 shows schematically a perspective view of an X-ray imaging system 500 with variable source-image distance. The imaging system 500 is a so-called digital interventional X-ray system 500 or C-arm system 500.

The X-ray imaging system 500 comprises an arc-shaped and/or semi-circular C-arm 502, wherein on a first end 501 of the C-arm 502 an X-ray source 504 for emitting X-ray photons is arranged. On a second end 503 of the C-arm 502 an X-ray detector 100 with an anti-scatter device 10 is arranged. The anti-scatter device 10 is generally arranged and configured for absorbing secondary X-ray photons, i.e. scattered photons. A distance between the first end 501 and the second end 503 of the C-arm 502 can be varied. Accordingly, a source-image-distance between the source 504 and the detector 100 can be varied as indicated by arrow 506 in FIG. 1.

The imaging system 500 further comprises a movable table 505 for supporting a patient.

The X-ray detector 100 and/or the anti-scatter device 10 are described in more detail in subsequent figures.

Figure 2:
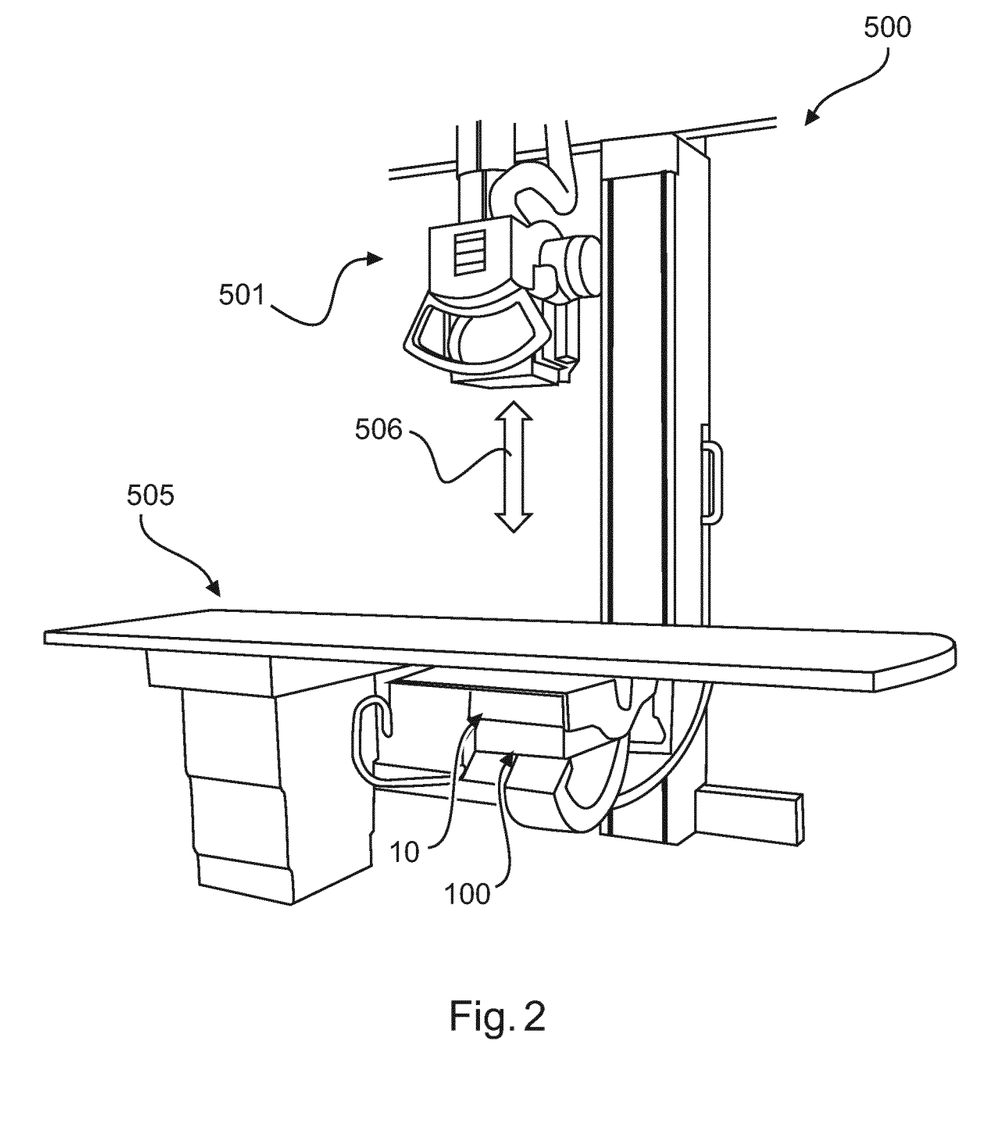

FIG. 2 shows schematically a perspective view of an X-ray imaging system 500 with variable source-image distance. The imaging system 500 is a so-called digital X-ray radiography system 500. If not stated otherwise, the X-ray imaging system of FIG. 2 comprises the same elements and features as the imaging system of FIG. 1.

In contrast to the imaging system of FIG. 1, the X-ray detector 100 and the anti-scatter device 10 of the imaging system of FIG. 2 are arranged below and/or underneath the table 505 and the X-ray source 501 is arranged above the table 505.

Also with the imaging system 500 of FIG. 2 the source-image-distance can be varied as indicated by the arrow 506.

Figure 3A:
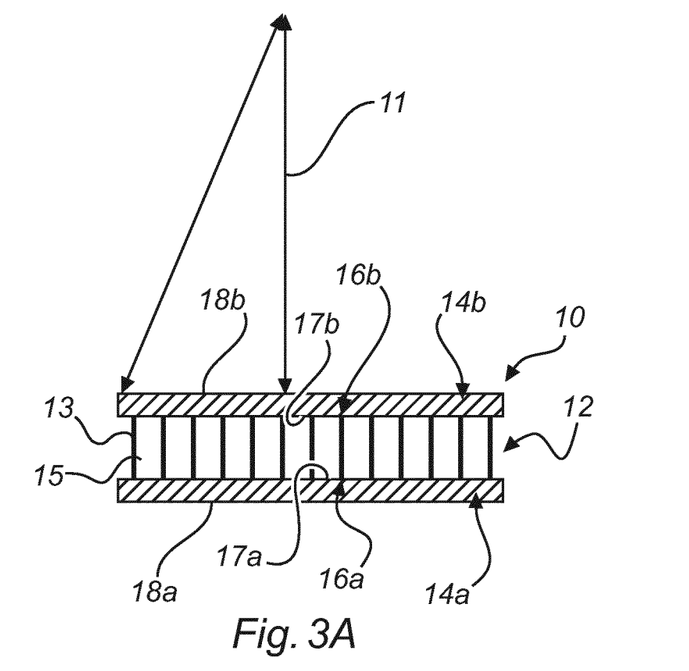
FIGS. 3A to 3C show schematically an anti-scatter device for an X-ray detector according to an embodiment.
Figure 3B:
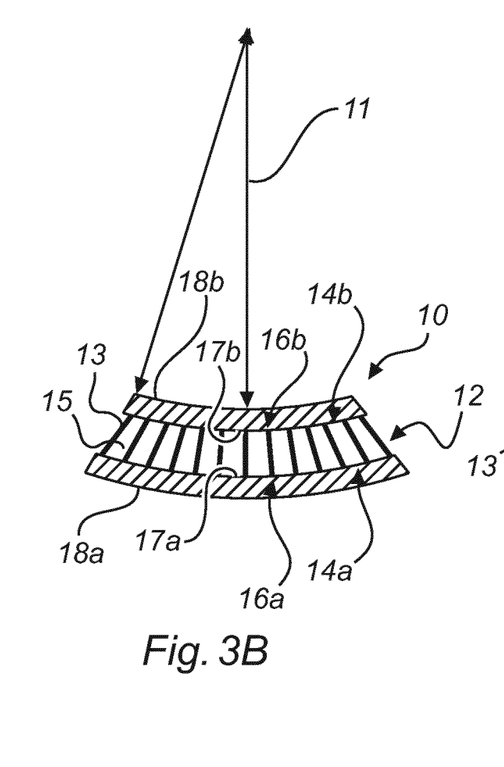
Figure 3C:
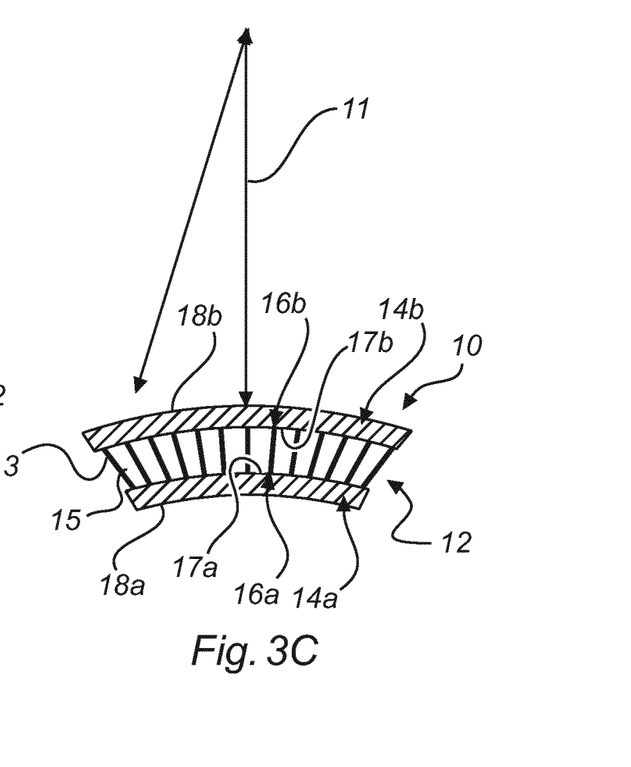

FIGS. 3A to 3C show schematically an anti-scatter device 10 according to an embodiment. Particularly, the anti-scatter device 10 may refer to a variable focus anti-scatter device 10 for an X-ray detector 100.

The anti-scatter device 10 comprises an anti-scatter grid 12 with a plurality or slats 13 and/or lamellae 13. The slats 13 may be arranged in several rows and/or columns, thereby forming an array of slats 13. The slats 13 may comprise any material suitable for absorbing photons, e.g. X-ray photons, such as Pb, Mo and/or W. The slats 13 may be spaced apart and/or separated from each other by interspacers 15 arranged between directly neighboring slats 13. The interspacers 15 may be pliable and/or comprise X-ray transparent and pliable interspacer material, such as e.g. fiber material and/or polymer material. The slats 13 may thus be embedded in a matrix of interspacer material forming the interspacers 15. However, the slats 13 may also be separated by air. Accordingly, the interspacer material may be air.

Further, the anti-scatter device 10 comprises a cover element 14a arranged on a side 17a of the anti-scatter grid 12 and a further cover element 14b arranged on a further side 17b of the anti-scatter grid 12, wherein the side 17a opposes the further side 17b. Therein, the slats 13 are arranged between the cover element 14a and the further cover element 14b. More specifically, a first end 16a of each of the slats 13 is mechanically coupled and/or attached to the cover element 14a and/or to a side of the cover element 14a. Moreover, a further end 16b of each of the slats 13 is mechanically coupled and/or attached to the further cover element 14b and/or to a side of the further element 14b. The ends 16a and/or the further ends 16b of the slats 13, thus, extend transversely from the cover element 14a to the further cover element 14b. The ends 16a and/or the further ends 16b may be glued, welded, soldered and/or otherwise attached to the cover element 14a and/or to the further cover element 14b, respectively.

Generally, the cover element 14a and/or the further cover element 14b may have a plate-like structure and refer to a cover plate, respectively, between which the slats 13 are arranged in a sandwich-like structure.

At least the cover element 14a comprises an electroactive polymer material such as e.g. Polyvinylidene-Fluoride and/or Polytrifluorovinyl. Generally, electroactive polymer material is expandable by applying a voltage, an electric field, a potential and/or a potential difference. Further, electroactive polymer material is elastically deformable, i.e. when the voltage is reduced and/or no voltage is applied, the material may shrink back to its original shape and/or size.

As a consequence of the electroactive polymer material contained in the cover element 14a, a dimension of the cover element 14a may be changed and/or increased by applying a voltage to the cover element 14a and/or to the electroactive polymer material contained therein. In other words, the cover element 14a may be expanded in size and/or length by applying the voltage and/or an extension of the cover element 14a may be induced by applying the voltage. Further, when the voltage is applied and the cover element 14a is stretched, a distance between the ends 16a of the slats is changed and/or increased and a focusing distance 11 of the anti-scatter device 10 is thereby changed, altered and/or adjusted.

Apart from changing, altering and/or adjusting the focusing distance 11, also at least a part of the anti-scatter device 10 may be bended when the voltage is applied to the cover element 14a. In other words, a radius of a curvature of the anti-scatter device 10 and/or an outer surface thereof may be changed by applying the voltage to the cover element 14.

As the electroactive polymer material may generally only expand under the influence of the voltage, also the further cover element 14b may comprise electroactive polymer material, which allows bending of the anti-scatter device in at least two opposite directions.

In order to apply the potential and/or the voltage to the cover element 14a, the anti-scatter device 10 comprises an electrode 18a connected to the cover element 14a and/or to the electroactive polymer material contained therein. In order to apply the potential and/or the voltage to the further cover element 14b, the anti-scatter device 10 comprises a further electrode 18b connected to the further cover element 14b and/or to the electroactive polymer material contained therein. The electrode 18a and/or the further electrode 18b may be flat and/or plane electrodes connecting an area of the cover element 14a and the further cover element 14b, respectively. However, the electrodes 18a, 18b may alternatively only locally connect to the respective cover element 14a, 14b.

Generally, the cover elements 14a, 14b may expand proportional to an increase of the voltage applied to the electrodes 18a, 18b, respectively. Further, by reducing the applied voltage, the corresponding cover element 14a, 14b may shrink proportional to the voltage reduction. Thus, the size of the cover elements 14a, 14b may be varied by varying the amount and/or level of voltage applied to the respective electrode 18a, 18b.

In FIG. 3A no voltage is applied to the cover element 14a and the further cover element 14b. Accordingly, the anti-scatter device 10 is flat and may have e.g. a focal distance 11 and/or a focusing distance 11 and/or focal length 11 of about 1000 mm. in FIG. 3B a voltage is applied to the cover element 14a, thereby inducing an extension in lateral direction, i.e. transversely to a longitudinal extension direction of the slats 13. Application of the voltage results in an increase of the distances between the ends 16a of the slats 13 and thus in an increase of a radius of a curvature of the anti-scatter device 10. As a consequence, the focusing distance 11 is reduced to about 800 mm. In contrast, in FIG. 3C a voltage is applied to the further cover element 14b and no voltage or a smaller voltage is applied to the cover element 14a. Thus, the anti-scatter device 10 is bended in opposite direction with respect to FIG. 3B, i.e. a sign of the curvature may be reversed, and a distance between the further ends 16b of the slats 13 is increased. In FIG. 3C, the focusing distance of the anti-scatter device may be about 1200 mm.

In the following, various aspects, features and/or elements of the anti-scatter device 10 are summarized. The anti-scatter device 10 comprises cover elements 14a, 14b containing electro-active polymer material such as PVDF and/or PTFV, and electrodes 18a, 18b are attached to the cover elements 14a, 14b, respectively. Putting a potential difference on the electrodes 18a, 18b may then steer lateral dimensions of the cover elements 14a, 14b and induce a curvature of the anti-scatter grid 12 and/or the anti-scatter device 10. Because an interior of the anti-scatter grid 12 comprises slats 13 and/or lamellae 13, the stiffness for the curvature and/or bending in one direction is much weaker than for a perpendicular and/or transverse direction. Accordingly, the anti-scatter device 10 and/or the anti-scatter grid 12 may preferentially curve along the weaker direction, which may be transverse to the longitudinal extension direction of the slats 13. This curvature may influence the position of the slats 13 and therefore the focal distance 11 of the anti-scatter grid 12 and/or the anti-scatter device 10 is changed. As an example an initially focused anti-scatter device grid is shown in FIG. 3A, which can be curved into a smaller focal distance 11 shown in FIG. 3B or into a larger focal distance 11 shown in FIG. 3C. It is preferable to start with a flat anti-scatter grid 12 and/or a flat anti-scatter device 10 with some pre-existing focus 11 close to a center of the source-image-distance range and curve the anti-scatter grid 12 and/or the anti-scatter device 10 only weakly to obtain either a smaller focal distance 11 by positive curvature and a larger focal distance 11 by negative curvature to prevent the anti-scatter grid from cracking under constant tension due to creep of the interior components.

Generally, an interior of the anti-scatter grid 12 may be flexible, at least a part of the slats 13 and an electro-active polymer material and/or the cover elements 14a, 14b containing electroactive material may cover the anti-scatter grid 12 on two opposite sides. The cover elements 14a, 14b may cover the anti-scatter grid 12 like a film and/or foil. The length of the cover elements 14a, 14b can be finely tuned by applying a voltage across the electro-active polymer. The top layer, i.e. the further cover element 14b, may expand a predetermined percentage while the bottom layer, i.e. the cover element 14a preferable stays at a fixed length. This may lead to a bending of the anti-scatter grid 12 and/or the anti-scatter device 10 and induce the focal distance change.

If an unfocussed and/or flat anti-scatter device 10 is used, the radius of curvature of the anti-scatter device 10 may be made equal to the source-image-distance and it may be used for imaging systems 500 with a static curved X-ray detector 100 with a radius of the curvature equal to the source-image-distance. The bendability of the anti-scatter device 10 may then only be used to fix the anti-scatter device 10 in a static radius of curvature and the anti-scatter device 10 and/or the anti-scatter grid 12 may be under constant curvature.

If a focused anti-scatter device 10 and/or anti-scatter grid 12 is used with a nominal grid focus in the flat state in the range of the source-image-distance of an imaging system 500, the anti-scatter device 10 may be used in a flat mode when the source-image-distance is equal to the nominal focal distance 11 of the anti-scatter grid 12. When the medical application demands a different source-image-distance, the anti-scatter device 10 and/or anti-scatter grid 12 may be curved accordingly. The benefit here may be that the anti-scatter grid 12 may not be under constant curvature. Alternatively, it may be used with a source-image-distance equal to the nominal focusing distance 11, no voltages have to be used and possible creep or cracking of the anti-scatter device 10 and/or the anti-scatter grid 12 may be reduced.

It can be calculated that a required relative length change of the electro-active polymer and/or the cover elements 14a, 14b, respectively, may only be in the part per thousand range to induce a large focal distance change for usual nominal focal distances 11 and grid thicknesses.

The invention may be used in any fixed and/or mobile imaging system 500 in which the source-image-distance may be variable but known and/or measurable. Because the invention supplies an approach and/or a method to optimize the focal distance 11 of the anti-scatter grid 12 and/or the anti-scatter device 10 with respect to the actual source-image-distance, the anti-scatter grid 12 transmission may be much better at the edges of the source-image-distance range and a better image quality may be reached. Because the factor of source-image-distance range limitations is lifted, an anti-scatter grid 12 with a higher grid ratio may be selected which may yield an even better image quality for each of the possible source-image-distances.

An additional application may solve the problem that anti-scatter grids 12 and/or anti-scatter devices 10 may curve uncontrolled when a modest amount of heat is applied to them. This may be an issue in warm climates as the anti-scatter grid 12 and/or the anti-scatter device 10 may become so curved that it may no longer fit into the movable bucky system and the X-ray system 500 may crash.

The electro-active polymers and/or the cover elements 14a, 14b may also be used as sensors for measuring the curvature of the anti-scatter grid 12 and external voltages may then be used to flatten out the anti-scatter grid 12, so it may no longer be curved and its curvature will cause no problems in the imaging system 500.

Figure 4A:
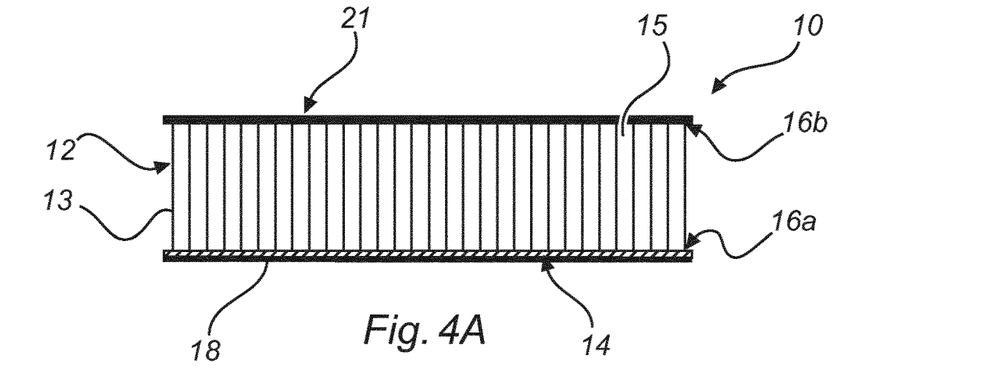
FIGS. 4A and 4B show schematically an anti-scatter device for an X-ray detector according to an embodiment.
Figure 4B:
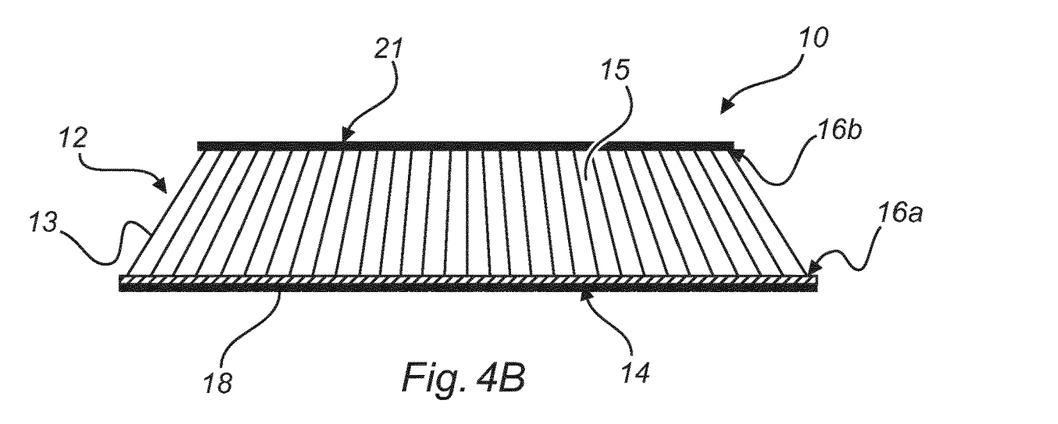

FIGS. 4A and 4B show schematically an anti-scatter device 10 for an X-ray detector 100 according to an embodiment. If not stated otherwise, the anti-scatter device 10 of FIGS. 4A and 4B comprise the same features and elements as the anti-scatter device 10 shown in previous figures.

In contrast to the anti-scatter device 10 shown in FIGS. 3A to 3C, the further cover element 21 of the anti-scatter device 10 shown in FIGS. 4A and 4B is rigid, stiff, non-deformable and/or does not comprise electroactive polymer material. Thus, also no further electrode connecting the further cover element 21 is required, i.e. the anti-scatter device 10 of FIGS. 4A and B comprises only one electrode 18 connecting the cover element 14, which comprises the electro-active polymer material.

In the configuration of the anti-scatter device 10 shown in FIG. 4A no voltage is applied to the electrode 18.

When in FIG. 4A a voltage is applied to the cover element 14 via the electrode 18, this results in an increase of a dimension, particularly a lateral dimension, of the cover element 14 as well as in an increase in the distance between the ends 16a of the slats 13. As shown in FIG. 4B, this results in a trapezoidal shape of the anti-scatter device 10 without necessarily inducing a curvature and/or bending of the anti-scatter device 10. The trapezoidal shape of the cover element may be adjusted and/or varied by varying the amount and/or level of the applied voltage.

Further aspects, features, functions and/or elements of the embodiment described above are summarized in the following. As e.g. indicated in FIGS. 4A and 4B, the anti-scatter grid 12 of the anti-scatter device 10 may be confined into a stiff frame and the interspacer material may be sufficiently pliable. This may result in a nearly flat anti-scatter grid 12 and/or anti-scatter device 10, in which the lamellae 13 and/or slats 13 themselves may move in a plane parallel to the cover element 14 in order to generate a variable focal/focusing distance.

Figure 5:
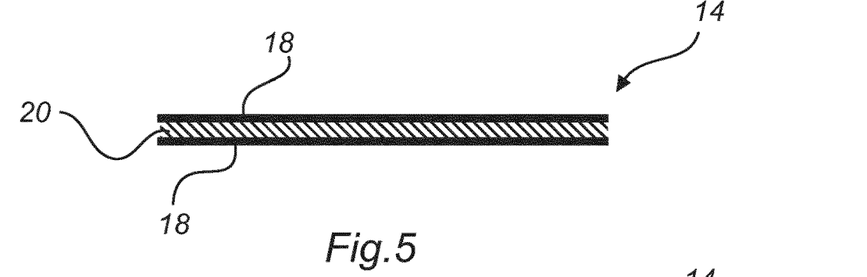
FIGS. 5 and 6 each show schematically a cover element for an anti-scatter device according to embodiments.

FIG. 5 shows schematically a cover element 14 for an anti-scatter device 10 according to an embodiment. If not stated otherwise, the cover element 14 shown in FIG. 5 comprises the same functions, features and elements as the cover elements 14a, 14b described in previous figures.

The cover element 14 shown in FIG. 5 comprises a layer 20 of electroactive polymer material and two electrodes 18, each covering an opposite side of the layer 20. When a voltage is applied and/or put across the electrodes 18, the cover element 14 may be actively shrunk in perpendicular (i.e. electrode) direction due to the electrostatic interaction between the electrodes and thereby expanding in a lateral direction and/or lateral directions, similar to a rubber band. Generally, by utilizing a plurality of electrodes 18 a required voltage for a certain extension may be reduced.

Figure 6:
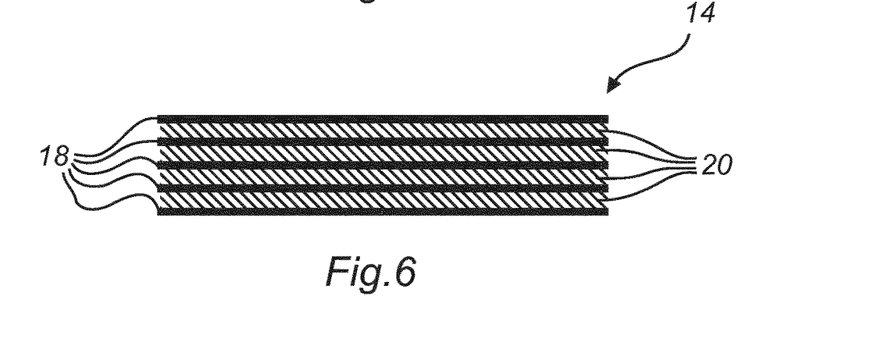

FIG. 6 shows schematically a cover element 14 for an anti-scatter device 10 according to an embodiment. If not stated otherwise, the cover element 14 shown in FIG. 6 comprises the same functions, features and elements as the cover elements 14, 14a, 14b described in previous figures.

The cover element 14 of FIG. 6 comprises in total five electrodes and four layers 20 of electroactive polymer material. Therein, the electrodes 18 and the layers 20 are alternately arranged and/or stacked on top of each other. Thus, the cover element 14 shown in FIG. 6 may refer to a multi-stack cover element 14.

When a voltage is applied and/or put across the electrodes 18, the cover element 14 may be expanded laterally and squeezed and/or refined in perpendicular direction. Generally, by utilizing a plurality of electrodes 18 the required voltage for a certain extension may be further reduced.

Figure 7:
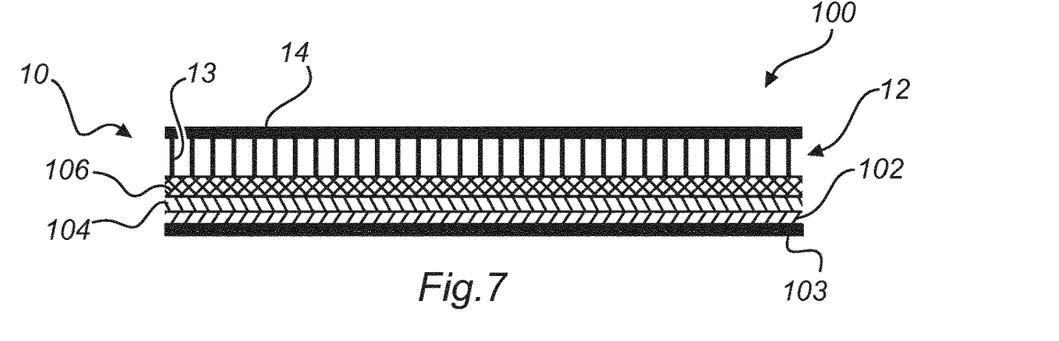
FIGS. 7 to 12 each show an X-ray detector according to embodiments.

FIG. 7 shows an X-ray detector 100 with an anti-scatter device 10 according to an embodiment. If not stated otherwise, the anti-scatter device 10 of the X-ray detector 100 shown in FIG. 7 comprises the same functions, features and elements as the anti-scatter devices 10 described with reference to previous figures.

The X-ray detector 100 of FIG. 7 comprises a flexible substrate foil 102. The substrate foil 102 may comprise e.g. polyimide, glass and/or silicon as substrate material. However, the substrate foil 102 may also comprise electroactive polymer material. For simplicity, various layers such as a detector cover, a scintillator encapsulation layer, a photodiode and pixel elements are not shown in detail.

The X-ray detector 100 further comprises an array and/or a layer of pixels 104 arranged on top of the substrate foil 102. The array 104 of pixels (for simplicity the pixels are not shown) is configured for detecting photons. The array 104 of pixels may for this purpose comprise at least one photo diode optically coupled to a scintillator 106, which is arranged on top of the array 104 and configured for converting X-ray photons into visible light, which may in turn be converted to a current and/or charge by the photo diode, which current and/or charge may then be detected by the array 104 of pixels.

On top of the scintillator 106 the anti-scatter device 10 is arranged, wherein the anti-scatter grid 12 and/or the slats 13 are in contact with the scintillator 106 and the cover element 14 forms an outer surface of the detector 100.

In another embodiment, the detector is of the direct-detection type and no scintillator is present. The anti-scatter grid and/or anti-scatter device is directly mounted on top of a layer which is sensitive for X-rays impinging onto this layer. In a structured electrode beneath this sensitive layer an electronic signal may be produced and/or generated. Such detectors may be made of Selenium, Silicon and/or any other semiconductor material layer which, e.g. when sufficiently thin, may also be bent.

Generally, the X-ray detector 100 shown in FIG. 7 may refer to a flexible detector 100, e.g. a detector on flexible foil 102, a detector on thin and/or flexible glass, or a detector on a thinned silicon substrate, which might be curved with either a fixed or a variable focus.

The X-ray detector 100 of FIG. 7 further comprises a layer 103 comprising electro-active polymer material, wherein the assembly of substrate foil 102, array 104, scintillator 106 and anti-scatter device 10 is arranged on top of the layer 103. In other words, layer 103 is arranged on an outer surface and forms an outer layer of the X-ray detector 100. The X-ray detector 100 shown in FIG. 7 may further comprise at least one electrode (also not shown for simplicity) for applying voltage to the cover element 14 and/or the layer 103 in order to induce an extension of the cover element 14 and/or the layer 103, thereby inducing a curvature of the entire detector 100. Accordingly, the scintillator 106 and the array 104 may be flexible enough to follow the curvature of the anti-scatter grid 12 and/or of the anti-scatter device 10.

By way of example, the X-ray detector 100 may have a dimension of about 30 cm by 40 cm, the anti-scatter device 10 and/or the anti-scatter grid 12 may have a thickness of about 1.5 mm to 3 mm, the scintillator 106 may have a thickness of about 0.3 mm to 0.6 mm, and the detector 104 may have a thickness of about 0.02 mm to about 0.2 mm and the substrate foil 102 may have a thickness of about 0.5 mm to about 1 mm.

Moreover, the cover element 14 may have a total thickness of about 0.5 mm to about 1 mm, a voltage of about 50 kV may be applied, and the electroactive polymer may be a PVDF/PTFE copolymer.

It should be noted that an X-ray detector 100 may be provided, which does not comprise the anti-scatter device 10, but which may comprise the layer 103 with electroactive material. Such detector 100 may then be bended and/or curved by applying voltage to the electroactive polymer material of the layer 103.

Further, it should be noted that layer 103 may be combined with the substrate foil 102. For instance, substrate foil 102 may be replaced by the layer 103.

Figure 8:
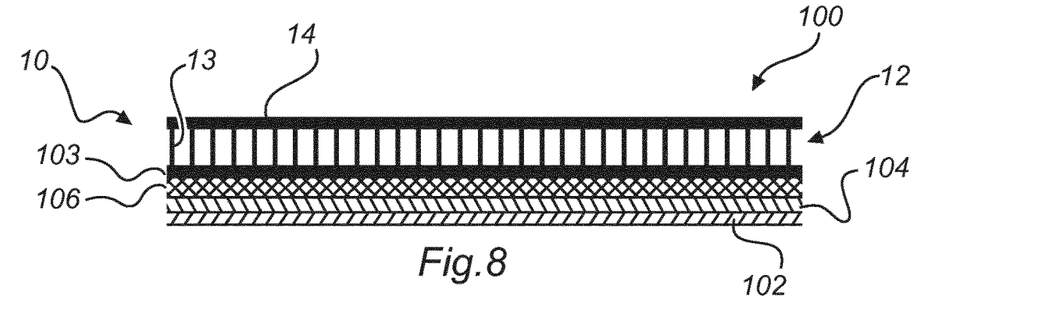

FIG. 8 shows an X-ray detector 100 with an anti-scatter device 10 according to an embodiment. If not stated otherwise, the anti-scatter device 10 of the X-ray detector 100 shown in FIG. 8 comprises the same functions, features and elements as the anti-scatter devices 10 described with reference to previous figures, and the X-ray detector 100 shown in FIG. 8 comprises the same functions, features and elements as the X-ray detector 100 of FIG. 7.

Further, the X-ray detector 100 of FIG. 8 comprises a layer 103, e.g. a flexible foil layer 103, with electroactive polymer material, which layer 103 is arranged between the anti-scatter grid 12 and the scintillator 106. The layer 103 and/or the cover element 14 may be connected to electrodes 18 (not shown) in order to bend the X-ray detector 100.

Figure 9:
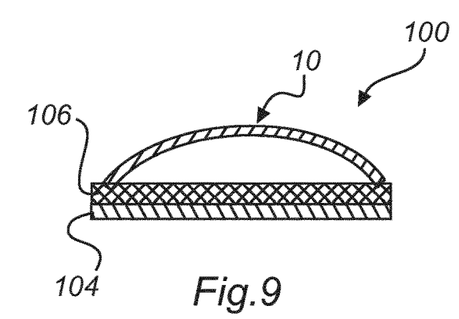

FIG. 9 shows an X-ray detector 100 with an anti-scatter device 10 according to embodiment. If not stated otherwise, the anti-scatter device 10 of the X-ray detector 100 shown in FIG. 9 comprises the same functions, features and elements as the anti-scatter devices 10 described with reference to previous figures. Moreover, if not stated otherwise, the X-ray detector 100 shown in FIG. 9 comprises the same functions, features and elements as the X-ray detectors 100 described with reference to previous figures.

As can be seen in FIG. 9, the array of pixels 104 and the scintillator 106 are flat and/or straight and only the anti-scatter device 10 is curved by applying voltage to the respective cover elements 14a, 14b (not shown in FIG. 9), wherein a center of the curvature is on an opposite side of the scintillator 106 and the array 104 as the anti-scatter device 10.

Figure 10:
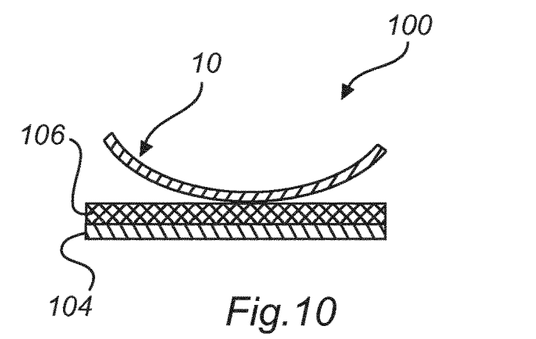

FIG. 10 shows an X-ray detector 100 with an anti-scatter device 10 according to embodiment. If not stated otherwise, the anti-scatter device 10 of the X-ray detector 100 shown in FIG. 10 comprises the same functions, features and elements as the anti-scatter devices 10 described with reference to previous figures. Moreover, if not stated otherwise, the X-ray detector 100 shown in FIG. 10 comprises the same functions, features and elements as the X-ray detectors 100 described with reference to previous figures.

As can be seen in FIG. 10, the array 104 of pixels and the scintillator 106 are flat and/or straight and only the anti-scatter device 10 is curved by applying voltage to the respective cover elements 14a, 14b (not shown in FIG. 10), wherein a center of the curvature is on the same side of the scintillator 106 and the array 104 as the anti-scatter device 10.

Figure 11:
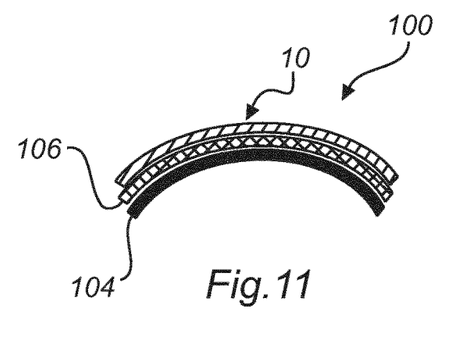

FIG. 11 shows an X-ray detector 100 with an anti-scatter device 10 according to embodiment. If not stated otherwise, the anti-scatter device 10 of the X-ray detector 100 shown in FIG. 11 comprises the same functions, features and elements as the anti-scatter devices 10 described with reference to previous figures. Moreover, if not stated otherwise, the X-ray detector 100 shown in FIG. 11 comprises the same functions, features and elements as the X-ray detectors 100 described with reference to previous figures.

As can be seen in FIG. 11, the array of pixels 104 and the scintillator 106 are flexible and the entire stack of array 104, scintillator 106 and anti-scatter device 10 is curved by applying voltage to the respective cover elements 14a, 14b (not shown in FIG. 11). Accordingly, the invention may be used to produce anti-scatter grids 12 with a well-defined curvature to fit the curvature of the detector 100. For such grids 12 a flat unfocused grid interior may be beneficial and the grid focus may be purely induced by the curvature of the anti-scatter grid 12.

Figure 12:
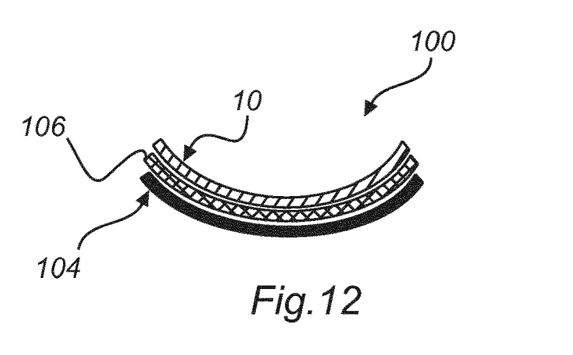

FIG. 12 shows an X-ray detector 100 with an anti-scatter device 10 according to embodiment. If not stated otherwise, the anti-scatter device 10 of the X-ray detector 100 shown in FIG. 12 comprises the same functions, features and elements as the anti-scatter devices 10 described with reference to previous figures. Moreover, if not stated otherwise, the X-ray detector 100 shown in FIG. 12 comprises the same functions, features and elements as the X-ray detectors 100 described with reference to previous figures.

The X-ray detector 100 shown in FIG. 12 basically corresponds to the detector 100 of FIG. 11, wherein the curvature is reversed, e.g. by applying a voltage to another cover element 14a, 14b as explained in detail with reference to FIGS. 3A to 3C.

Figure 13:
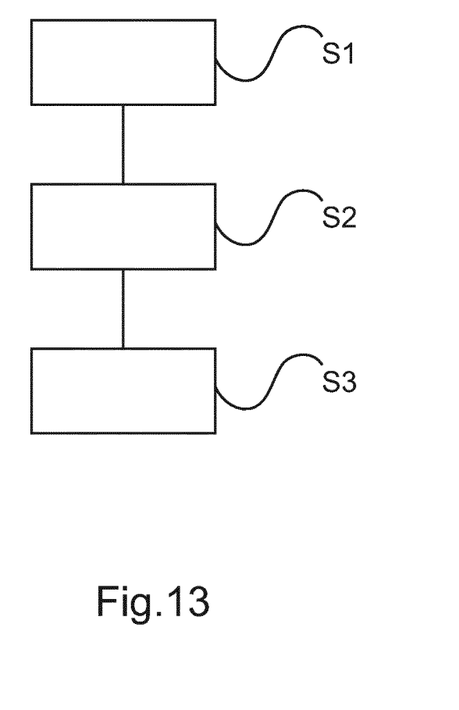
FIG. 13 shows a flowchart illustrating steps of a method for producing an anti-scatter device 10 according to an embodiment.

FIG. 13 shows a flowchart illustrating steps of a method for producing an anti-scatter device 10 according to an embodiment.

In a first step S1 an anti-scatter grid 12 with a plurality of slats 13 for absorbing X-rays is provided. The slats of the anti-scatter grid 12 may be spaced-apart from each other by pliable interspacer material or air.

In a second step S2 a cover element 14a is arranged on a side of the anti-scatter grid 12, such that the slats 13 extend transversely from the cover element 14a.

In a further step S3 ends 16a of the slats 13 are mechanically coupled to the cover element 14a, wherein the cover element 14a comprises an electroactive polymer material and wherein a dimension of the cover element 14a is changeable and/or increasable by applying a voltage to the electroactive polymer material, such that a distance between the ends 16a of the slats 13 is changeable, controllable and/or increasable by applying the voltage.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An anti-scatter device for an X-ray detector, the anti-scatter device comprising:
    an anti-scatter grid with a plurality of slats for absorbing X-rays; and
    a cover element arranged on a side of the anti-scatter grid;
    wherein ends of the slats are coupled to the cover element;
    wherein the cover element comprises an electroactive polymer material; and
    wherein a dimension of the cover element is changeable by applying a voltage to the electroactive polymer material, such that a distance between the ends of the slats is changeable by applying the voltage.

2. The anti-scatter device according to claim 1, wherein at least a part of the anti-scatter device is bendable by applying the voltage to the electroactive polymer material of the cover element.

3. The anti-scatter device according to claim 1, wherein the cover element comprises at least one layer of the electroactive polymer material; and/or wherein the cover element comprises at least one electrode for applying the voltage.

4. The anti-scatter device according to claim 1,
wherein the anti-scatter device comprises a plurality of layers and a plurality of electrodes; and
wherein the plurality of layers and the plurality of electrodes are alternately arranged.

5. The anti-scatter device according to claim 1, wherein the electroactive polymer material comprises at least one monomer selected from the group consisting of Vinylidene-Fluoride and Trifluorovinyl.

6. The anti-scatter device according to claim 1, wherein the cover element is formed as a foil.

7. The anti-scatter device according to claim 1, further comprising:
a further cover element;
wherein the anti-scatter grid is arranged between the cover element and the further cover element;
wherein further ends of the slats are coupled to the further cover element.

8. The anti-scatter device according to claim 7,
wherein the further cover element is rigid; and/or
wherein the further ends of the slats are fixed at the further cover element.

9. The anti-scatter device according to claim 7,
wherein the further cover element comprises electroactive polymer material; and
wherein a dimension of the further cover element is changeable by applying a voltage to the electroactive polymer material of the further cover element, such that a distance between the further ends of the slats is changeable by applying the voltage.

10. An X-ray detector comprising:
at least one anti-scatter device, wherein the at least one anti-scatter device comprises:
an anti-scatter grid with a plurality of slats for absorbing X-rays; and
a cover element arranged on a side of the anti-scatter grid;
wherein ends of the slats are coupled to the cover element;
wherein the cover element comprises an electroactive polymer material; and
wherein a dimension of the cover element is changeable by applying a voltage to the electroactive polymer material, such that a distance between the ends of the slats is changeable by applying the voltage.

11. The X-ray detector according to claim 10, further comprising:
a flexible substrate foil;
an array of pixels arranged on the substrate foil and configured for detecting X-rays; and
a scintillator arranged on the array of pixels;
wherein the anti-scatter device is arranged on the scintillator;
wherein the anti-scatter grid is arranged between the cover element of the anti-scatter device and the scintillator; and
wherein at least a part of the X-ray detector is bendable by applying the voltage to the electroactive polymer material of the cover element.

12. The X-ray detector according to claim 11,
wherein the substrate foil comprises electroactive polymer material; and
wherein the X-ray detector is bendable by applying a voltage to the electroactive polymer material of the substrate foil.

13. The X-ray detector according to claim 11, further comprising:
a layer comprising electroactive polymer material.

14. A method for producing an anti-scatter device, the method comprising:
providing an anti-scatter grid with a plurality of slats for absorbing X-rays;
arranging a cover element on a side of the anti-scatter grid, such that the slats extend transversely from the cover element;
coupling ends of the slats to the cover element;
wherein the cover element comprises an electroactive polymer material; and
wherein a dimension of the cover element is changeable by applying a voltage to the electroactive polymer material, such that a distance between the ends of the slats is changeable by applying the voltage.

* * * * *